United States Patent
Ohtake et al.

(10) Patent No.: US 7,593,099 B2
(45) Date of Patent: Sep. 22, 2009

(54) METHOD AND DEVICE FOR CONFIGURATION EXAMINATION

(75) Inventors: Hideyuki Ohtake, Kariya (JP); Toshiharu Sugiura, Tokoname (JP)

(73) Assignee: Aisin Seiki Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 11/869,312

(22) Filed: Oct. 9, 2007

(65) Prior Publication Data
US 2008/0084554 A1 Apr. 10, 2008

(30) Foreign Application Priority Data
Oct. 10, 2006 (JP) .............................. 2006-276513

(51) Int. Cl.
*G01N 21/00* (2006.01)
(52) U.S. Cl. .................. 356/237.2; 356/237.1; 356/601
(58) Field of Classification Search .... 356/237.1–237.5
See application file for complete search history.

(56) References Cited

U.S. PATENT DOCUMENTS

| | | | |
|---|---|---|---|
| 6,556,306 B2 * | 4/2003 | Jiang et al. | 356/517 |
| 2002/0118371 A1 * | 8/2002 | Jiang et al. | 356/517 |
| 2005/0179905 A1 * | 8/2005 | Ohtake et al. | 356/450 |
| 2006/0146334 A1 * | 7/2006 | Cluff et al. | 356/455 |
| 2007/0296957 A1 * | 12/2007 | Fitzgerald et al. | 356/51 |
| 2008/0013071 A1 * | 1/2008 | Tsumura et al. | 356/51 |
| 2008/0137068 A1 * | 6/2008 | Ouchi et al. | 356/51 |
| 2008/0165355 A1 * | 7/2008 | Yasui et al. | 356/323 |

FOREIGN PATENT DOCUMENTS

JP 2005-43230 A 2/2005

* cited by examiner

*Primary Examiner*—Michael P Stafira
(74) *Attorney, Agent, or Firm*—Sughrue Mion, PLLC

(57) ABSTRACT

A method of examining a configuration of a sample includes the step of irradiating a terahertz pulsed light, which possesses a wavelength to transmit through the sample, to at least two different portions of the sample, the step of detecting at least two electric field amplitude-time resolved waveforms of the terahertz pulsed light transmitted through the first and second portions of the object to be examined, and the step of examining the configuration of the sample based upon phase information obtained from the electric field amplitude-time resolved waveforms detected.

6 Claims, 8 Drawing Sheets

METHOD AND DEVICE FOR CONFIGURATION EXAMINATION

CROSS REFERENCE TO RELATED APPLICATIONS

This application is based on and claims priority under 35 U.S.C. § 119 to Japanese Patent Application 2006-276513, filed on Oct. 10, 2006, the entire content of which is incorporated herein by reference.

FIELD OF THE INVENTION

The present invention generally relates to a method and a device for examining a configuration of an object manufactured by injection molding, compression molding, extrusion molding, or the like. More specifically, the present invention relates to a method and a device for irradiating an electromagnetic wave through a sample and examining a bump and a configuration of the sample by a change of the electromagnetic wave passing through the object.

BACKGROUND

Resin-made components are frequently employed as components of vehicles, digital products, or the like, in place of metal materials in order to reduce weight and cost. Particularly in vehicle components, various sensors are mounted on the vehicles for a high-function controlling of an engine. Therefore, it is no exaggeration to say that quality of configuration of the resin-made components plays a part for reliability of the vehicle. Further, in digital household electric appliances, tiny resin-made members mechanically play important roles, with a tide of miniaturization and integration. In addition, precision components, made of glass and ceramics, also play important roles in the components of the vehicle and of the digital household appliances. Accordingly, it is important to quantitatively evaluate defects in configuration of such components.

Members made of high polymer materials such as resin material and rubbers, and inorganic materials such as glass and ceramics are manufactured by extrusion molding, injection molding, and by compressive burning, for example. However, the members manufactured may include a stepped portion, a blister, a projection, a roughness, or the like.

Conventionally, such defective portions are detected by irradiating an electromagnetic wave (terahertz wave) with wavelength to pass through an object and then examining a change of transparent intensity of the electromagnetic wave after transmitting through the object. For example, one of such defect detecting method and device is disclosed in Japanese Patent No. 2005-43230A (hereinafter, referred to as reference 1).

The above-described defect detecting device detects a defect of an elongated member (such as a pipe member) with uniform cross section on the basis of a change of transparent intensity of an electromagnetic wave passing through the elongated member. However, the transparent intensity of the electromagnetic wave is influenced by a defect inside of the object and compositional homogeneity of composition of the object, for example. Therefore, greater noise may be generated, and sensitivity and precision for defect detection may be lowered. Further, the transparent intensity is integrated in accordance with a direction where the electromagnetic wave is irradiated. Therefore, measurement of the defect from an irradiated direction may not be obtained. Still further, according to the known method and device, existence or nonexistence of the defect at the uniform cross section of the elongated member is qualitatively evaluated. However, the defect of an object without a pipe-shaped configuration may not be quantitatively evaluated. Accordingly, size and shape as three-dimensional configuration of the defect may not be quantitatively evaluated.

A need thus exists for a method and a device for configuration examination which are not susceptible to the drawback mentioned above.

SUMMARY OF THE INVENTION

According to an aspect of the present invention, a method of examining a configuration of a sample includes a step of irradiating a terahertz pulsed light, which possesses a wavelength to transmit through the sample, to at least two different portions of the sample. The at least two different portions has a first portion and a second portion. The method of examining a configuration of the sample further includes a step of detecting each electric field amplitude-time resolved waveform of the terahertz pulsed light transmitted for every part through plurals portions of the sample, and a step of examining the configuration of the sample based upon phase information obtained from the electric field amplitude-time resolved waveforms detected. Further according to another aspect of the present invention, a configuration examination device includes a laser light source, a light dividing portion, a light-delay controlling portion, a terahertz pulsed light generating portion, and a light-irradiating portion. The laser light source generates short pulsed laser light. The light dividing portion divides the short pulsed laser light into a pump light and a probe light. The light-delay controlling portion controls a time delay of the pump light or the probe light both divided by the light dividing portion from the short pulsed laser light. The terahertz pulsed light generating portion is optically pumped by the pump light divided by the light dividing portion and generates the terahertz pulsed light with the wavelength to transmit through the object to be examined. The light-irradiating portion irradiates the terahertz pulsed light generated by the terahertz pulsed light generating portion to a portion of the sample. The configuration examination device further includes a moving portion, a light-receiving portion, a detecting portion, and a configuration judging portion. The sample is placed on the moving portion and is moved thereby. Accordingly, the light-irradiating portion irradiates the terahertz pulsed light to another portion of the sample. The light-receiving portion receives the terahertz pulsed lights transmitted through the portions of the sample moved by the moving portion. The detecting portion detects the electric field amplitude-time resolved waveform of the terahertz pulsed light received by the light-receiving portion with the probe light. The configuration judging portion judges the configuration of the sample with the phase information of the electric field amplitude-time resolved waveform.

BRIEF DESCRIPTION OF THE DRAWINGS

The foregoing and additional features and characteristics of the present invention will become more apparent from the following detailed description considered with reference to the accompanying drawings, wherein.

DETAILED DESCRIPTION

Figure 1:
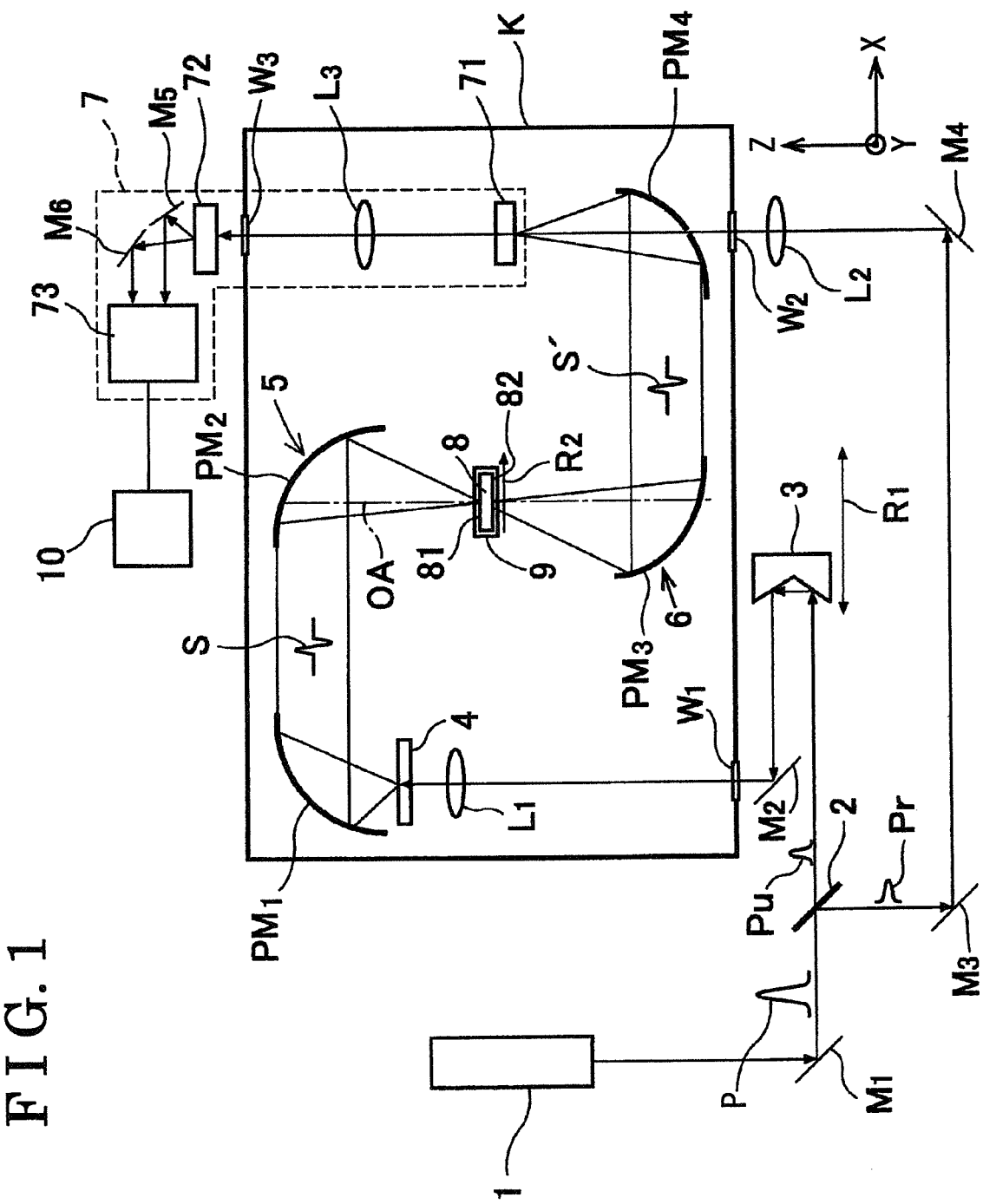
FIG. 1 is a schematic overview illustrating a configuration examination device according to the present invention.

An embodiment of the present invention will be described hereinafter with reference to attached drawings. Components possessing the same general configuration between each drawing will be denoted with the same reference numerals and duplicated explanation will be omitted herein.

FIG. 1 is a schematic overview illustrating a configuration examination device according to the present invention. As illustrated in FIG. 1, the configuration examination device includes a laser light source 1, a light dividing portion 2, a light-delay controlling portion 3, a terahertz pulsed light generating portion 4, a light-irradiating portion 5, a moving portion 9, a light-receiving portion 6, a detecting portion 7, and a configuration judging portion 10. With reference to FIG. 1, M1 to M6 represent planar mirrors and L1 to L3 represent lenses. Additionally, PM1 to PM 4 represent off-axis parabolic mirrors and W1 to W3 represent windows. A housing K isolates light paths of terahertz pulsed light from an exterior of the housing K. An interior of the housing K is in a vacuum condition or in a nitrogen atmosphere for preventing the terahertz pulsed light from being absorbed by molecules consisting the air.

The laser light source 1 is represented by a mode-locked fiber laser apparatus, for example. The laser light source 1 generates short pulsed laser light P of which pulse width is between femtoseconds and picoseconds. In addition, a small-sized fiber laser is employed as one of the example of the mode-locked fiber laser apparatus, a small sized-fiber laser which possesses central wavelength in 780 nm (nanometer) zone, an average output power of 20 mW (milliwatt), and a pulse repetition frequency of 50 MHz (megahertz).

The light dividing portion 2 is represented by a beam splitter or a wedged plate, for example. The light dividing portion 2 divides the short pulsed laser light P into pump light Pu and probe light Pr.

The light-delay controlling portion 3 is represented by a device attached to a stage (not illustrated) which moves a corner mirror (not illustrated) in a direction of an arrow R1, i.e., in a direction of an axis X, for example. The light-delay controlling portion 3 scans delay time by controlling a path length of the pump light Pu. Additionally, according to the configuration examination device of this embodiment, the light-delay controlling portion 3 is provided in a light path of the pump light Pu. Alternatively, the light-delay controlling portion 3 may be provided in a light path of the probe light Pr.

The terahertz pulsed light generating portion 4 is represented by a dipole antenna configured by a low temperature-grown GaAs (Gallium Arsenide), an InSb (Indium Antimonide) crystal, or an InAs (Indium Arsenide) semiconductor crystal, for example. The terahertz pulsed light generating portion 4 is optically pumped by the pump light Pu, which is divided by the light dividing portion 2, and generates the terahertz pulsed light S with a wavelength to transmit through a sample 8.

The light-irradiating portion 5 is configured by off-axis parabolic mirrors PM1 and PM2, for example. The light-irradiating portion 5 collimates terahertz pulsed light S generated by the terahertz pulsed light generating portion 4, and then gathers the terahertz pulsed light S to around a surface 81 of two parallel surfaces 81 and 82 of the sample 8 so that a light axis OA is oriented perpendicularly relative to the two surfaces 81 and 82 of the sample 8, i.e., in a direction of an axis Z. For example, when a beam diameter of the terahertz pulsed light S collimated by the off-axis parabolic mirror PM1 is assigned as about 15 mm and the terahertz pulsed light S with the diameter of 15 mm is gathered to the off-axis parabolic mirror PM2 with a focal length of 150 mm, a diameter of a gathered light becomes to 2 mm. Accordingly, a numerical aperture of the light-irradiating portion 5, i.e., a numerical aperture NA1 of terahertz pulsed light S irradiating to the sample 8, is about 0.05.

The moving portion 9 is represented by a stage moving in the direction of the axis X, for example. The moving portion 9 moves the sample 8 in a direction of an arrow R2, i.e., in the direction of the axis X. Accordingly, a position of the sample 8, where the light-irradiating portion 5 irradiates the terahertz pulsed light, is changed from one portion (first portion) to another portion (second portion).

The light-receiving portion 6 is configured by off-axis parabolic mirrors PM3 and PM4, for example. The light-receiving portion 6 collimates transmitted terahertz pulsed light S', which corresponds to the terahertz pulsed light S after passing through the sample 8. Further, the light-receiving portion 6 gathers the transmitted terahertz pulsed light S' to the detecting portion 7. A focal length of the off-axis parabolic mirror PM3 is 150 mm and an aperture thereof is 50 mm. Numerical aperture NA2 of the light-receiving portion 6 is about 0.16.

Figure 2:
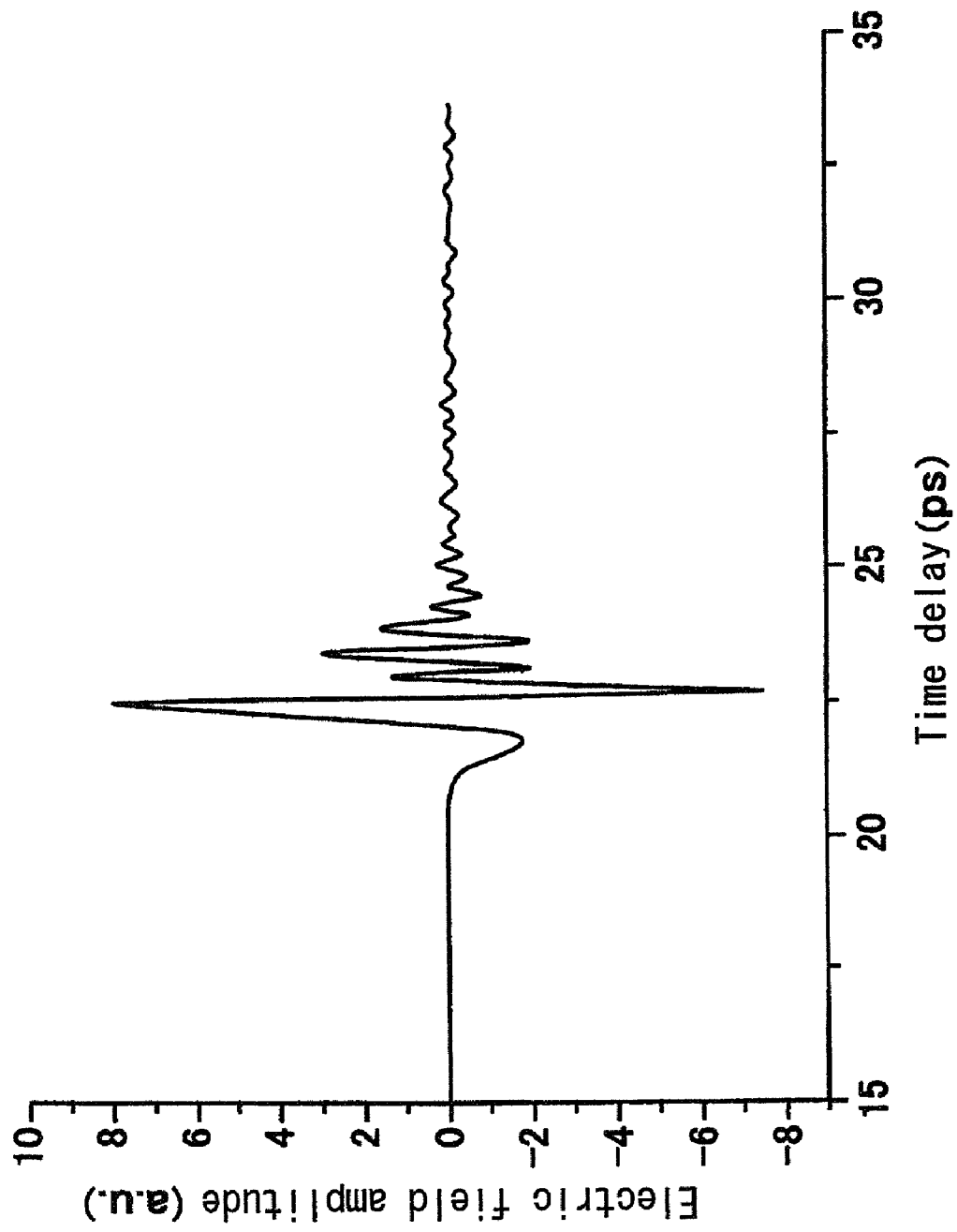
FIG. 2 is a graph illustrating an example of an electric field amplitude-time resolved waveform.

The detecting portion 7 includes a ZnTe (Zinic Telluride) crystal 71 as an electro optic crystal (EO crystal), a Walston prism 72, and a balance detector 73. The detecting portion 7 detects an electric field amplitude-time resolved waveform of the terahertz pulsed light, which is received by the light-receiving portion 6, with the probe light (Pr), which is divided by the dividing means 2. More specifically, the balance detector 73 extracts a polarization-rotational amount of the probe light Pr by means of a differential amplifying mechanism, a polarization-rotational amount which is generated by a complicated refraction induced by the ZnTe crystal 71. Accordingly, a signal inputted from the detecting portion 7 to the configuration judging portion 10 which will be described later, includes the electric field amplitude-time resolved waveform, as illustrated in FIG. 2. FIG. 2 is a graph illustrating the electric field amplitude-time resolved waveform of the terahertz pulsed light S which transmitted through the sample 8 (i.e., of the transmitted terahertz pulsed light S'). Additionally, for example, the ZnTs crystal 71 may be replaced by the low temperature-grown GaAs and may include a current amplifier for amplifying photovoltaic current of the probe light Pr generated when the terahertz pulsed light S is detected.

The configuration judging portion 10 is represented by a personal computer, for example. The configuration judging portion 10 receives the signal amplified by a lock-in amplifier (not illustrated), and then, judging a configuration of the sample 8 from phase information obtained from the electric field amplitude-time resolved waveform as illustrated in FIG. 2. The members respectively representing the portions 2 to 10 of the examination device and a configuration thereof are not limited to the described above. Alternatively, other members, components, and configurations may be employed as far as satisfying the function described above.

Figure 3:
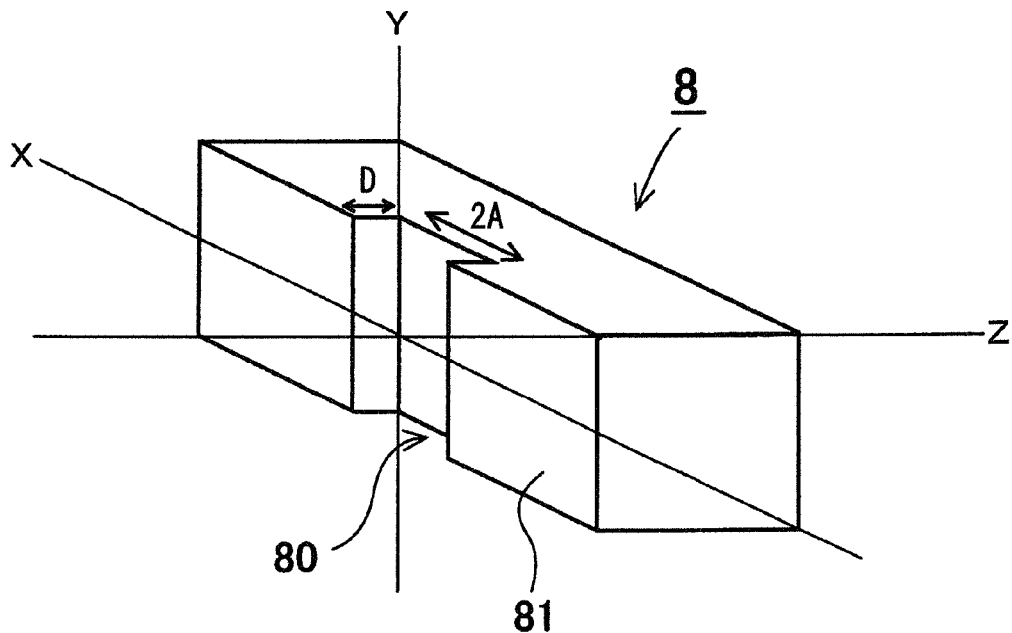
FIG. 3 is an enlarged perspective view illustrating an sample and the vicinity thereof.
Figure 4:
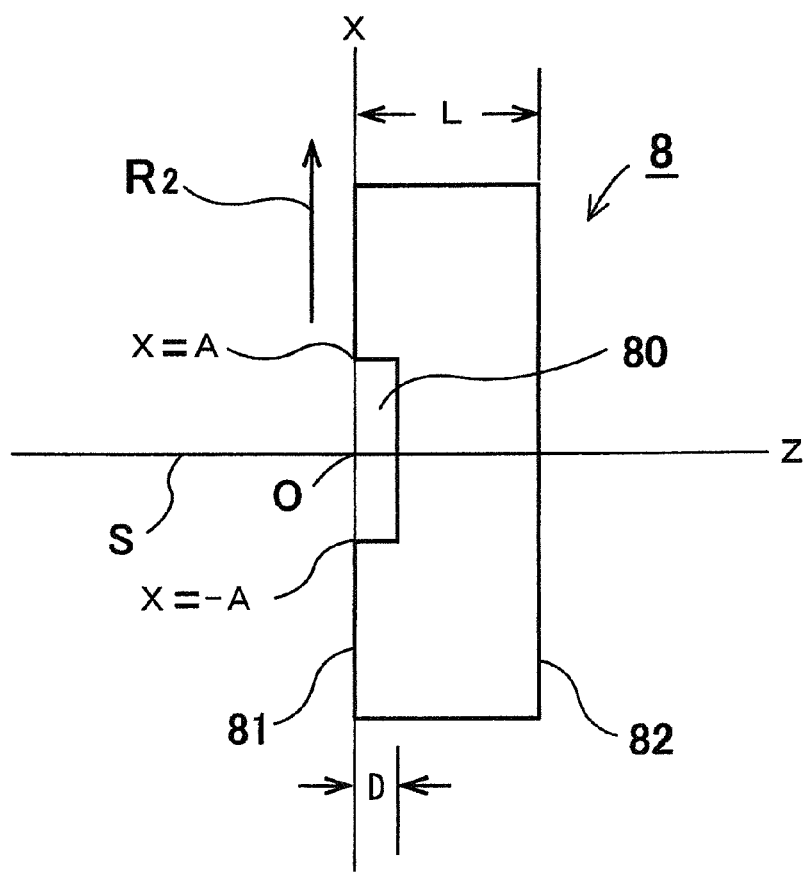
FIG. 4 is an enlarged plan view illustrating the sample shown from X and Z axis.

Next, a theory for examining configuration of an sample 8 with the configuration examination device according to the embodiment will be described hereinafter. FIG. 3 is an enlarged perspective view illustrating the sample 8 and the vicinity thereof in FIG. 1. FIG. 4 is an enlarged plane view illustrating the sample 8 shown from X and Z axis. Measurement of the sample 8 in the light axis OA (in the direction of the axis Z) is assigned as L. The sample 8 includes a concave portion 80, of which step-height in the direction of axis Z is assigned as D and of which step-width in the direction of axis X is assigned as 2A. Here, a first corner portion of the concave portion 80 is assigned as A and a second corner portion of the concave portion 80 is assigned as −A.

Figure 5:
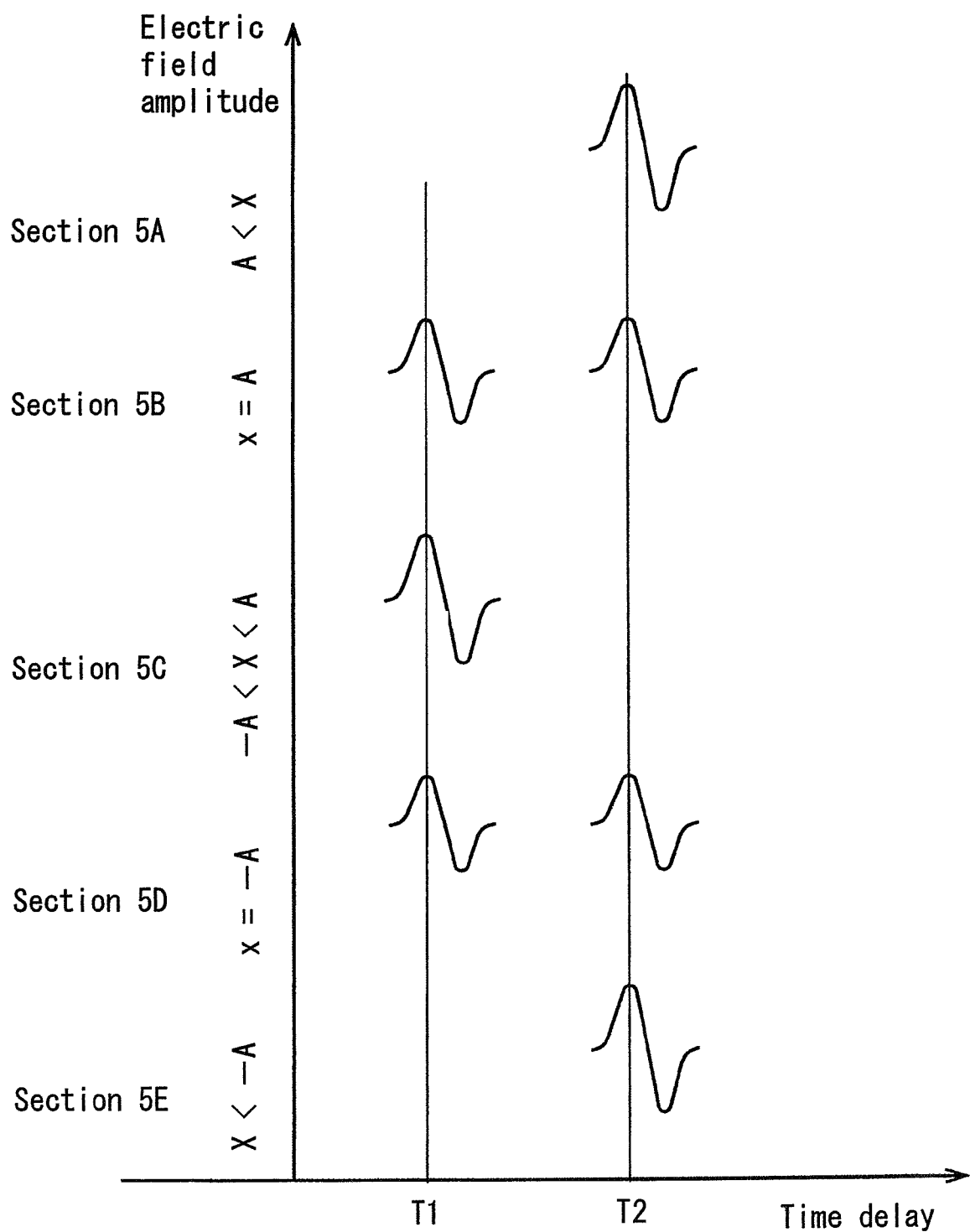
FIG. 5 is a schematic view illustrating electric field amplitude-time resolved waveforms in a condition where the sample is moved in a direction of an arrow R2 in FIG. 1 and an irradiating position of a terahertz pulsed light is changed.

FIG. 5 is a schematic view illustrating the electric field amplitude-time resolved waveform (hereinafter, referred to as signal) in a condition where the sample 8 is moved by the moving portion 9 in the direction of the arrow R2 (i.e., in a direction of the axis X) and an irradiating position X (irradiating portion) of the terahertz pulsed light S is changed. Section 5C in FIG. 5 illustrates a waveform in a condition where the irradiating position X of the terahertz pulsed light S is within the first and second corner portions A and −A, i.e., when the irradiating position X is within the concave portion 80 with step-width 2A of the sample 8 (−A<X<A). In such condition, the terahertz pulsed light S passes through over the concave portion 80 of the sample 8. Section 5A in FIG. 5 illustrates a waveform in a condition where the irradiating position X of the terahertz pulsed light S is upper than the first corner portion A in the direction of axis X shown in FIG. 4 (A<X). Section 5E in FIG. 5 illustrates a waveform in a condition where the irradiating position X of the terahertz pulsed light S is lower than the second corner portion −A in the direction of axis X shown in FIG. 4 (X<−A). In such conditions, the terahertz pulsed light S passes through over portions with the thickness L of the sample 8 but without passing the concave portion 80. Section 5B in FIG. 5 illustrates a waveform in a condition where the irradiating position X is at the first corner portion A of the concave portion 80, while the section 5D illustrates a waveform in a condition where the irradiating position X is at the second corner portion −A of the concave portion 80 (X=±A). In such conditions, the terahertz pulsed light S partially passes through the portion with thickness L and partially passes through the concave portion 80, of the sample 8. Signals which appear at T1 in a transverse axis (i.e., a time axis) in FIG. 5 represent signals when the terahertz pulsed light S transmitted through the concave portion 80 with the step-height D (i.e., a portion with a thickness (L−D) of the sample 8). On the other hand, signals which appear at T2 in the transverse axis in FIG. 5 represent signals when the terahertz pulsed light S transmitted through the portion with the thickness L of the sample 8.

At first, a relationship between delay time difference ΔT1 (delay time difference between T1 and T2 (T2−T1)) and step-height D of the concave portion 80 will be described hereinafter. The relationship between the delay time difference ΔT1 represents one of the phase information of the electric field amplitude-time resolved waveform.

Generally, propagation time of the terahertz pulsed light is obtained by dividing the path length thereof by speed of light C. Additionally, when a refractive index of a propagation medium is assigned as N and a propagation distance is assigned as L, the path length of the terahertz pulsed light is obtained by multiplying N with L (NL). Accordingly, a refractive index of the sample 8 corresponds to the propagation medium N, and the thickness of the sample 8 corresponds to the propagation distance L. Further, the step-height of the concave portion 80 of the sample 8 is assigned as D, as aforementioned. Accordingly, the delay time difference ΔT1 is obtained by an equation (1) described as follows:

$$\Delta T1 = D(N-1)/C. \tag{1}$$

Consequently, when the refractive index N of the sample 8 is already known, the step-height D of the concave portion 80 in the direction of the axis Z is obtained by the equation (1). Further, with reference to FIG. 5, step-width 2A of the stepped portion 80 in the direction of the axis X is obtained by moving the sample 8 in the direction of the axis X and then detecting a position where the signal appearing at T1 disappears.

Figure 6:
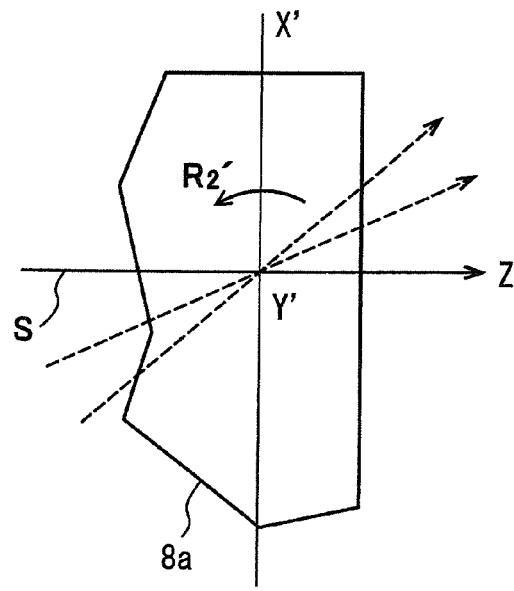
FIG. 6 is a plan view illustrating an asymmetric-shaped sample to be examined by being rotary-scanned.

In addition, as illustrated in FIG. 6, a configuration or an asymmetric-shaped sample 8a is measured by rotating the asymmetric-shaped sample 8a around an axis Y', i.e., around a direction of an arrow R2'. In other words, CT measurement is performed. Here, the axis Y' shown in FIG. 6 is perpendicular to an axis X' (i.e., the axis Y' is perpendicular to the drawing itself).

Generally, light is refracted when passing a boundary surface with different refractive index. For example, according to the present embodiment, when the sample 8 includes inside thereof a defective portion such as a void (gap), the terahertz pulsed light S may not reach the detecting portion 7 because of lens operation performed by a refractive index difference between the defective portion and non-defective portion or a total reflection caused by a critical angle.

Figure 7:
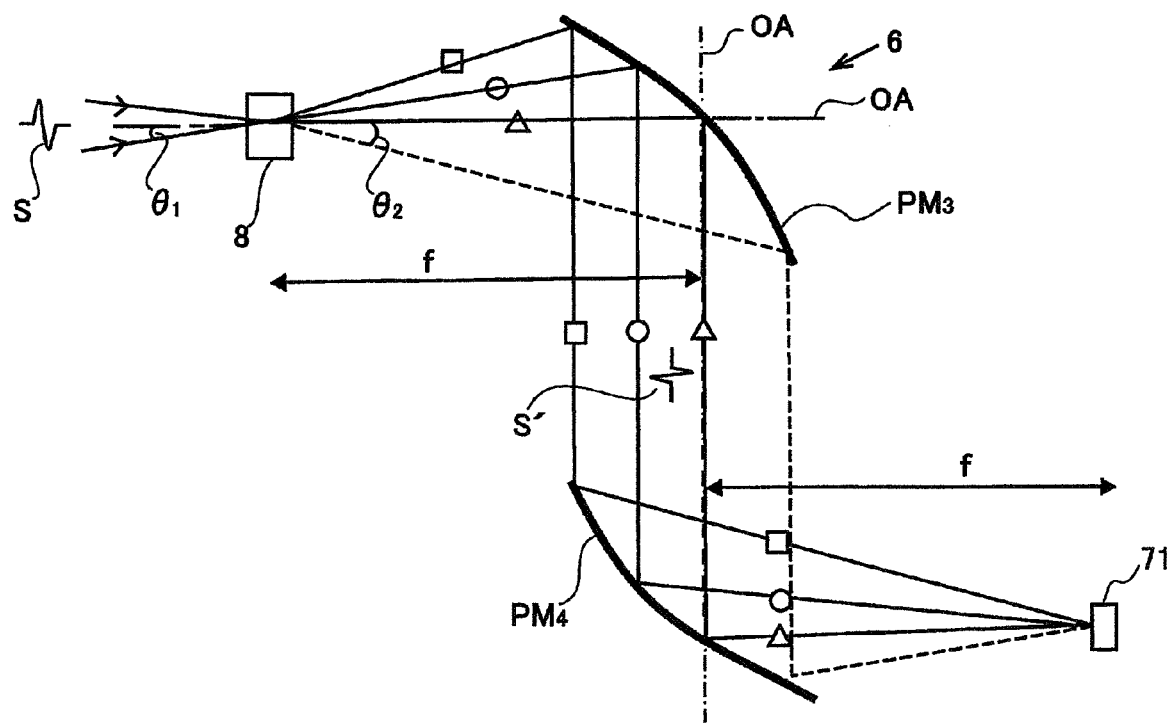
FIG. 7 is a schematic view illustrating ray trajectories of the terahertz pulsed light transmitted from the sample to an EO crystal of a detecting portion.

In order to reduce an influence of the lens operation and light scattering occurred by the critical angle and the refraction both which are generated by the sample 8, the numerical aperture NA2 of the light-receiving portion 6 is made greater than the numerical aperture NA1 of the light-irradiating portion 5, as will be described hereinafter. FIG. 7 is a schematic view illustrating ray trajectories of the terahertz pulsed light S transmitted from the sample 8 to the ZnTe crystal 71 (EO crystal) of the detecting portion 7. With reference to FIG. 7, θ1 represents a half angular aperture of the terahertz pulsed light S gathered and irradiated to the sample 8, and θ2 represents a half angular aperture of the light-receiving portion 6. Further, represents a ray which transmits through the outer most light path from among the light paths of the terahertz pulsed light S (reference lights) in a case where the sample 8 is not arranged, and Δ represents a ray transmitting the light axis OA. Still further, □ represents an outer most ray which is refracted at an entrance surface or the boundary surface of the defective portion inside, for example, and each arrow represents focal length of the light-receiving portion 6. The numerical aperture NA1 of the terahertz light transmitting through the sample 8 is obtained by an equation "NA1=N sin θ1". In the same manner, the numerical aperture NA2 of the light-receiving portion 6 is obtained by an equation "NA2=N sin θ2". As described above, when the numerical aperture NA1 is assigned as 0.05 and the numerical aperture NA2 is assigned as 0.16, i.e., when the numerical aperture NA2 is greater than the numerical aperture NA1 (NA1<NA2), the ray refracted (□) is received by the light-receiving portion 6 and enters into the ZnTe crystal 71 (EO crystal). Accordingly, the terahertz pulsed light S transmitted through the sample 8 is received and detected without losses. Further, configuration of the sample 8 can be effectively examined without being influenced by the lens operation nor the light scattering occurred by the critical angle and the refraction.

In addition, the off-axis parabolic mirrors PM3 and PM4 are employed to the light-receiving portion 6. Each of the refracted ray □, the ray Δ passing the light axis, and the ray passing through the outer most light path from among the light paths of terahertz lights (reference lights) is guided from a focus point of the off-axis paraboloid mirror PM3. Therefore, when the three rays □, Δ and are gathered onto the ZnTe crystal 71 (EO crystal) of the detecting portion 7 by means of the off-axis parabolic mirror PM4, the three rays □, Δ and surely reach an identical focus point of the ZnTe crystal 71 (EO crystal) 71 without any phase differences. Accordingly, the configuration of the sample 8 can be examined with high precision.

In a case were surface of the sample 8 is not a flat surface, for example, the terahertz pulsed light S, which passes through the sample 8, is refracted in a direction different from a direction of an original light axis because of its inherent configuration and refractive index. In addition, in a case where the sample 8 includes an extraneous, a defective portion, or a void, etc, of which sizes are almost similar to the wavelength, the terahertz pulsed light S receives a light scattering influence in the direction different from the direction of the original light axis. In such a case, the terahertz pulsed light influenced by the refraction and the scattering may not reach to a detecting portion of a detecting element, i.e., when an electro-optic crystal (EO crystal) is employed for detecting the configuration of the sample 8, the terahertz pulsed light S may not reach a specific portion of the crystal which the probe light Pr (short pulsed laser light) for the detection is illuminated, while when a photoconductive antenna is employed, the terahertz pulsed light S may not reach a gap portion of the photoconductive antenna which the probe light Pr irradiates. However, as described above, according to an arrangement of the present invention, each of light collection optics and collimation of the terahertz pulsed light S, after passing through the sample 8, includes a numerical aperture to receive refraction light and scattered light. Further, with the arrangement of the present invention, each light path length of the terahertz pulsed light refracted and scattered is identical in any route. Accordingly, the scattered and refracted terahertz pulsed light and the terahertz pulsed light passing through the light axis reach the detecting portion of the detecting element concurrently.

Figure 8:
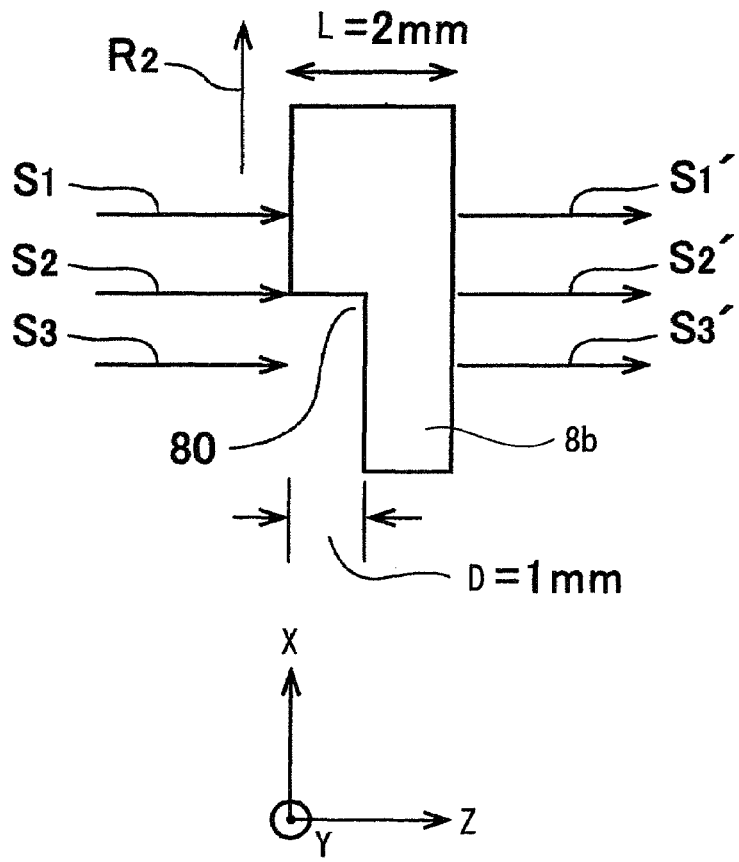
FIG. 8 is an sample utilized for a demonstration experiment.

As a demonstration experiment of the examination theory, the inventor prepared a sample 8b as shown in FIG. 8 and performed an experiment hereinbelow. The sample 8b utilized in the experiment was a block of polybutylene terephthalate (PBT) including a stepped portion 80 with a step-height D being 1 mm.

Figure 9:
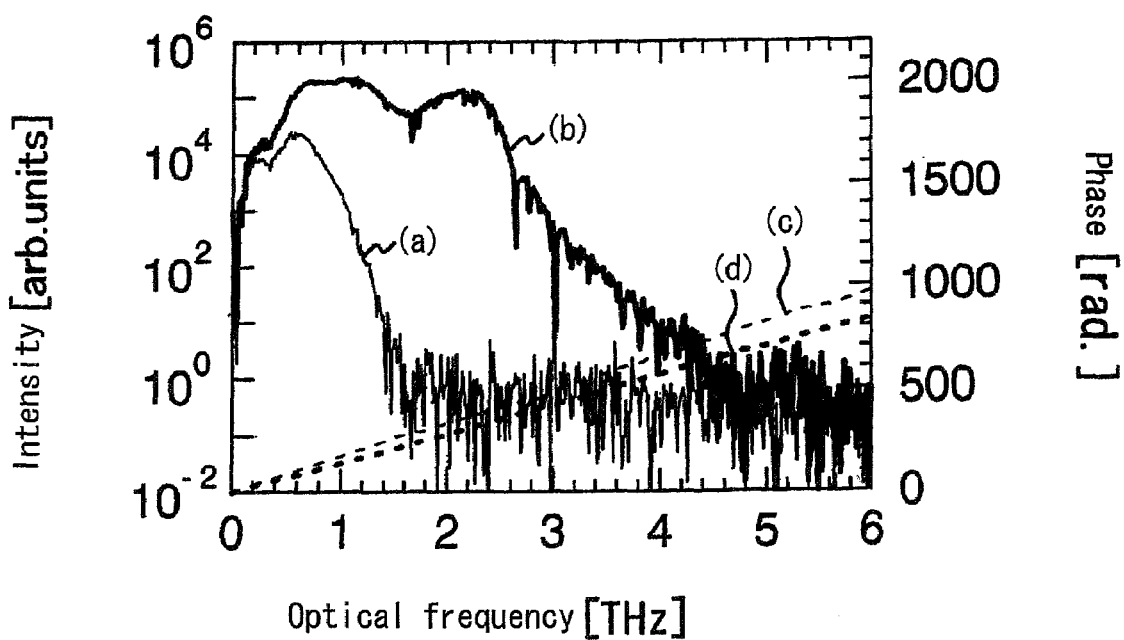
FIG. 9 is a graph illustrating spectral intensities and phases obtained by Fourier-transforming the electric field amplitude-time resolved waveform of the terahertz pulsed light detected by a detecting portion, respectively.

At first, refractive index of the sample 8b was measured by means of the configuration examination device shown in FIG. 1. FIG. 9 is a graph illustrating spectral intensities and phases obtained by Fourier-transforming the electric field amplitude-time resolved waveform of the terahertz pulsed light S detected by the detecting portion 7, respectively. With reference to FIG. 9, a waveform (b) illustrates a terahertz pulsed light spectrum (reference light spectrum) before setting the sample 8b. A waveform (a) illustrates a terahertz light spectrum (signal light spectrum) after setting the sample 8b and passing therethrough. Further, a dotted line (d) illustrates reference light phase and a dotted line (c) illustrates signal light phase.

Figure 10:
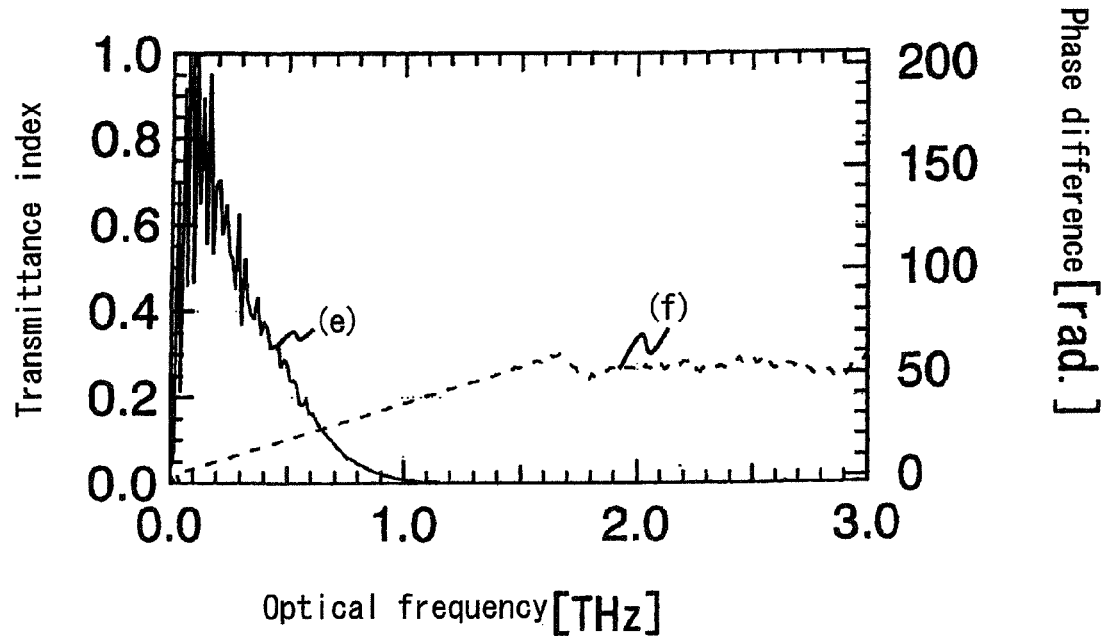
FIG. 10 is a graph illustrating transmittance rate and phase difference, both which are calculated with reference to FIG. 9.

FIG. 10 is a graph illustrating transmittance index (e) and phase difference (f), both which are calculated with reference to FIG. 9. The transmittance index was obtained by dividing signal light intensity with reference light intensity, ((signal light intensity)/(reference light intensity)). The phase difference was obtained by subtracting the reference light phase from the signal light phase ((signal light phase)−(reference light phase)). With reference to FIG. 10, when optical frequency was equal to, or larger than 1 THz (i.e., the wavelength was equal to, or lower than 300 μm), the inventor found that the transmittance index was almost zero, i.e., the terahertz pulsed light rarely passed through the sample. More specifically, with reference to FIGS. 9 and 10, when the optical frequency was around 1.4 THz, the signal was reduced lower than noise level. Additionally, as illustrated with the waveform (f), the phase difference was successively changed. However, when the optical frequency was around 1.6 THz (i.e., the wavelength was about 200 μm), the noise was increased, which attributed to that the signal intensity necessary for an analysis was not obtained because the transmittance index was too low. Accordingly, the inventor found that the terahertz pulsed light with optical frequency being lower than 1.4 THz passed through the sample 8b as described above. On the other hand, even in lower optical frequency region, when the optical frequency was equal to, or lower than 0.2 THz (the wavelength was equal to or greater than 1.5 mm), the transmittance rate partly became greater than 1.0. That could be attributed to that an analysis process was not available because there were some parts where the signal light intensity or the reference light intensity was low. Accordingly, a subsequent analysis range was determined between 0.2 THz to 1.4 THz.

Figure 11:
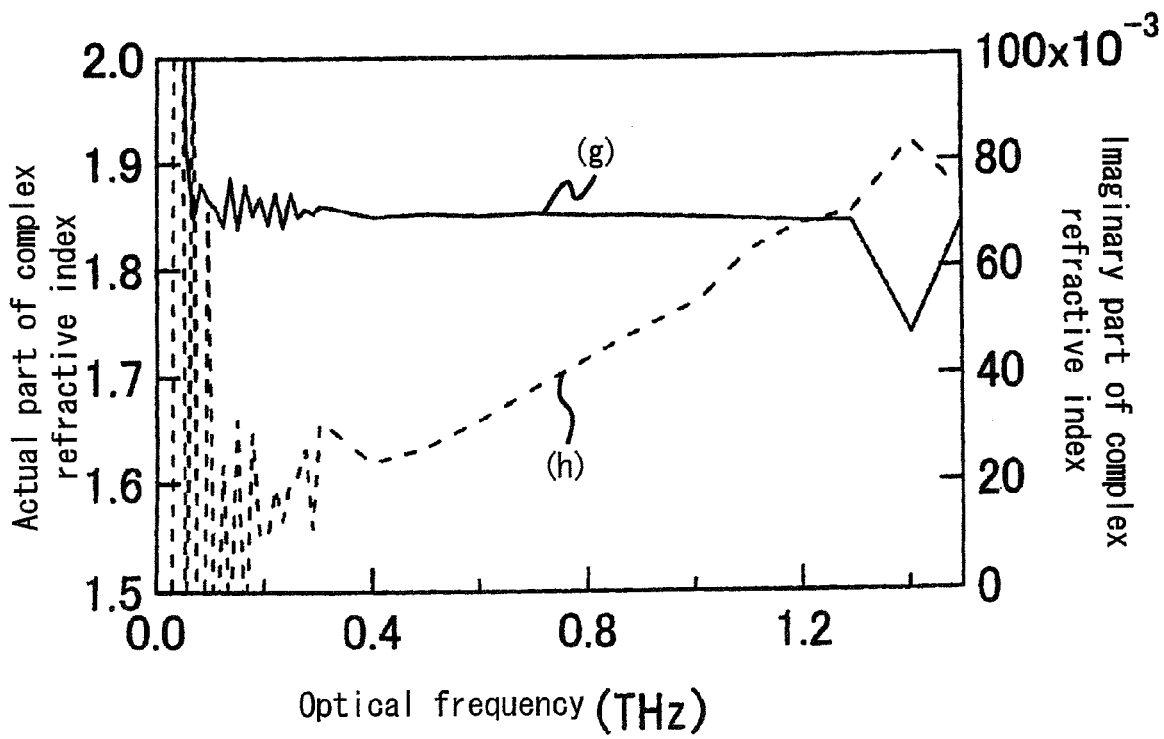
FIG. 11 is a graph illustrating complex refractive index calculated on the basis of a result found in FIG. 10.

FIG. 11 is a graph illustrating a complex refractive index calculated on the basis of a result found in FIG. 10. An actual part (g) represents the refractive index, and an imaginary part (h) represents an absorbing coefficient. With reference to FIG. 10, the refractive index N of the sample according to the embodiment was about 1.85 when the optical frequency was between 0.2 THz and 1.4 THz (when the wavelength was between 200 μm and 1.5 mm). According to a result described above, an example of the terahertz pulsed light, of which wavelength was from 200 μm to 1.5 mm because of the influence of the noise and transmittance rate of the PBT high polymer material, was shown. In addition, however, in a case where the noise was reduced and other materials were employed as the sample 8b, refractive index of various high polymer materials were considered to be about two or three times as much even when the wavelength for the examination was enlarged from 10 μm (10 THz) to 3 mm (0.1 THz).

Generally, resin material includes transmittance bandwidth at terahertz light bandwidth (0.1 THz to 10 THz). However, the transmittance bandwidth is different in accordance with each resin material. The PBT material described above includes the bandwidth with 0.2 THz to 1.4 THz, which is an example where the transmittance bandwidth is comparably narrow. When general resin material is employed as the sample, it is preferable that the transmittance bandwidth be from 0.1 THz to 10 THz.

The complex refractive index changes according to physical property anomalous of the sample 8, such as deterioration of the material, infusion of foreign objects, disorder of tissue, and so on. On the contrary, the physical property anomalous may be detected by the complex refractive index.

Next, as illustrated in FIG. 8, the configuration examination practiced in a condition where the sample was moved by the moving portion 9 and an irradiating portion of the terahertz pulsed light S with 2 mm of spot diameter was changed. More specifically, at first, terahertz pulsed light S1 was irradiated to a portion of the sample with 2 mm in thickness and passed therethrough. Then, terahertz pulsed light S'1, which corresponded to the terahertz pulsed light S1 after passing through the portion with 2 mm in thickness, was detected. Afterward, the sample was moved. Then, terahertz pulsed light S2 was irradiated to the stepped portion 80, and the terahertz pulsed light S'2, which corresponded to the terahertz pulsed light S2 after passing the stepped portion 80, was detected. Further then, terahertz pulsed light S3 was irradiated to a portion of the stepped portion 80 with 1 mm in thickness and passed therethrough. Afterward, terahertz pulsed light S'3, which corresponded to the terahertz pulsed light S3 after passing through the portion with 1 mm in thickness, was detected.

Figure 12:
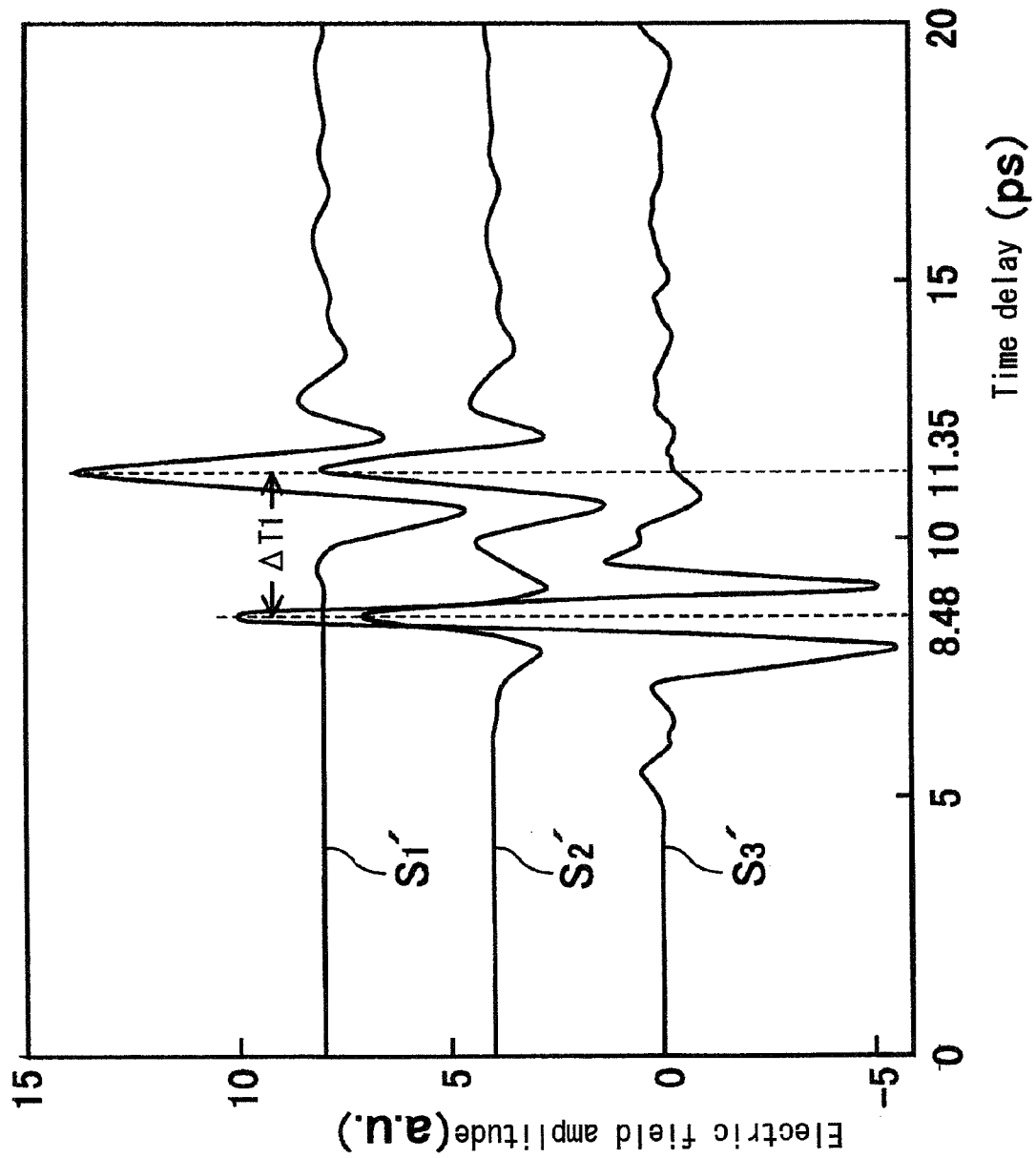
FIG. 12 is a graph illustrating electric field amplitude-time resolved waveform of the terahertz pulsed light after irradiated to the sample in the demonstration experiment.

FIG. 12 is a graph illustrating electric field amplitude—time resolved waveforms of the above described terahertz pulsed lights S'1 to S'3. When the delay time difference $\Delta T1$ was assigned as 2.87 ps ($\Delta T1=2.87$ ps) with reference to FIG. 12 and the refractive index of a propagation medium N was assigned as 1.85 (N=1.85), the step-height D was obtained as 1 mm from the equation (1). In other words, it was proved that the step-height, which corresponds to a measurement of the stepped portion 80 of the sample in the direction of the light axis, can be obtained by the phase information of the electric field amplitude-time resolved waveform of the terahertz pulsed light passing through the sample.

As illustrated above, the phase information of the terahertz pulsed light passing through the sample directly appears on the time resolved waveform of the terahertz pulsed light passing through the sample. Therefore, according to the present invention, the stepped portion and the configuration of the sample can be examined by measuring the time resolved waveform but without processing signals such as deconvolution.

Due to the above described method and device of the present invention, the phase information obtained from the electric field amplitude-time resolved waveform of the terahertz pulsed light S is greatly influenced by a light path of the terahertz pulsed light transmitted through the sample 8. Accordingly, detection precision for detecting the configuration of the sample 8 may be high.

Further, according to the present invention, the phase information is the delay time difference $\Delta T1$ between the time T1 when the terahertz pulsed light S transmits through the first portion of the sample and the time T2 when the terahertz pulsed light S transmits through the second portion of the sample (T2−T1).

As described above, the time difference $\Delta T1$ between the time T1 when the terahertz pulsed light S transmits through the first portion of the sample 8 and the time T2 when the terahertz pulsed light S transmits through the second portion of the sample 8 is greatly influenced by a difference of path lengths between the first portion and the second portion. Accordingly, a difference of configuration measurements (step-heights) between the first portion and the second portion may be detected with high precision.

Further according to the present invention, a numerical aperture NA2 of the light-receiving portion 6 is greater than a numerical aperture NA1 of the light irradiating portion 5.

As described above, the terahertz pulsed light S transmitted through the sample 8 is received by the receiving portion 6 with a large numerical aperture NA2. Accordingly, even when the terahertz pulsed light S is scattered because of a defect inside of the object, for example, it may be possible to efficiently receive the terahertz pulsed light S transmitted through the sample 8.

Further, when the terahertz pulsed light S is irradiated to a stepped portion 80 of the sample 8, a configuration of the stepped portion 80 may be examined by irradiating the terahertz pulsed light S once.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

The invention claimed is:

1. A method of examining a configuration of a sample having a pre-known refractive index, comprising the steps of;
    irradiating a terahertz pulsed light, which possesses a wavelength to transmit through the sample, to at least two different portions of the sample, the at least two different portions having a first portion and a second portion;
    detecting each electric field amplitude-time resolved waveform of the terahertz pulsed light transmitted for every part through plural portions of the sample; and
    examining the configuration of the sample based upon the pre-known refractive index of the sample and phase information obtained from the electric field amplitude-time resolved waveforms detected.

2. A method of examining a configuration of a sample according to claim 1, wherein the phase information includes a time difference between a time when the terahertz pulsed light transmits through the first portion of the sample and a time when the terahertz pulsed light transmits through the second portion of the sample.

3. A configuration examination device, comprising:
    a laser light source generating a short pulsed laser light;
    a light dividing portion dividing the short pulsed laser light into a pump light and a probe light;
    a light-delay controlling portion controlling a time delay of the pump light or the probe light both divided by the light dividing portion from the short pulsed laser light;
    a terahertz pulsed light generating portion optically pumped by the pump light divided by the light dividing portion and generating a terahertz pulsed light with a wavelength to transmit through a sample having a pre-known refractive index;
    a light-irradiating portion irradiating the terahertz pulsed light generated by the terahertz pulsed light generating portion to a portion of the sample;
    a moving portion placing the sample thereon and moving the sample, so that the light-irradiating portion irradiates the terahertz pulsed light to another portion of the sample;
    a light-receiving portion receiving the terahertz pulsed lights transmitted through the portions of the sample moved by the moving portion;

a detecting portion detecting the electric field amplitude-time resolved waveform of the terahertz pulsed light received by the light-receiving portion with the probe light; and a configuration judging portion judging the configuration of the sample using the pre-known refractive index thereof and the phase information of the electric field amplitude-time resolved waveform.

4. A configuration examination device according to claim 3, wherein numerical apertures of the light-receiving portion is greater than numerical apertures of the light-irradiating portion.

5. A configuration examination device according to claim 3, wherein the phase information is a time difference between a time when the terahertz pulsed light transmits through the first portion of the sample and a time when the terahertz pulsed light transmits through the second portion of the sample.

6. A configuration examination device according to claim 4, wherein the phase information is a time difference between a time when the terahertz pulsed light transmits through the first portion of the sample and a time when the terahertz pulsed light transmits through the second portion of the sample.

* * * * *